(12) United States Patent
Leight

(10) Patent No.: US 6,241,041 B1
(45) Date of Patent: Jun. 5, 2001

(54) MULTI-CONE EARPLUG AND METHOD OF FORMING AND USING

(75) Inventor: Howard S. Leight, Santa Monica, CA (US)

(73) Assignee: Bacou USA Safety, Inc., San Diego, CA (US)

( * ) Notice: Subject to any disclaimer, the term of this patent is extended or adjusted under 35 U.S.C. 154(b) by 0 days.

(21) Appl. No.: 08/297,399

(22) Filed: Aug. 29, 1994

Related U.S. Application Data

(63) Continuation-in-part of application No. 08/071,540, filed on Jun. 4, 1993, now abandoned.

(51) Int. Cl.$^7$ ........................................................ A61B 7/02

(52) U.S. Cl. ............................................................ 181/135

(58) Field of Search ..................................... 181/129, 130, 181/135; 128/152, 864, 867, 414; D24/106

(56) References Cited

U.S. PATENT DOCUMENTS

| D. 195,322 | 5/1963 | Hill | D24/106 |
|---|---|---|---|
| 2,246,737 | 6/1941 | Knudsen | 181/135 |
| 2,487,038 | 11/1949 | Baum | 181/135 |
| 4,055,233 | 10/1977 | Huntress | 181/135 |
| 4,867,149 | 9/1989 | Falco | 128/864 |
| 5,113,967 | 5/1992 | Killion et al. | 181/135 X |

Primary Examiner—Khanh Dang
(74) Attorney, Agent, or Firm—Leon D. Rosen

(57) ABSTRACT

An earplug is described, of the type which has an elongated stem (12, FIG. 2) and a plurality of hollow cone elements (20-24) each centered on the stem and spaced along a forward portion thereon, which has enhanced noise-blocking ability and which is easier to install and remove. Each element is in the shape of a hollow cone, and has a peripheral portion (32) that extends at an included angle (C) that is preferably about 60°, which results in wider area sealing of the peripheral portion of the cone elements against the ear canal of the wearer. The considerable included angle of the cone element peripheral portions, also facilitates the folding over of the peripheral portion of an element into a reverse configuration (32C, FIG. 7) during pullout of the earplug from the ear canal, to facilitate such pullout.

5 Claims, 2 Drawing Sheets

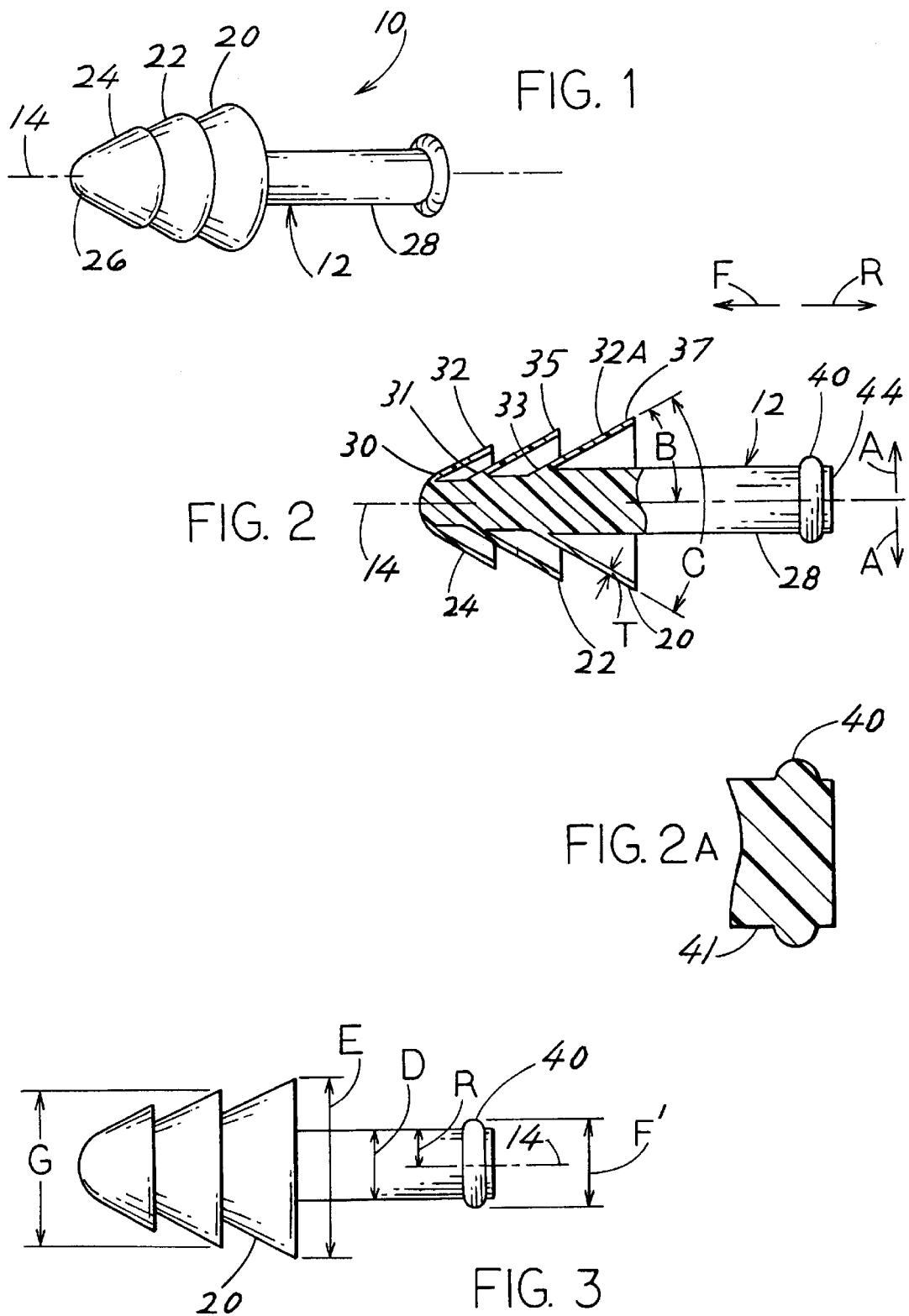

MULTI-CONE EARPLUG AND METHOD OF FORMING AND USING

CROSS-REFERENCE TO RELATED CASE

This is a continuation-in-part of Ser. No. 08/071,540 filed Jun. 4, 1993, now abandoned.

BACKGROUND OF THE INVENTION

One type of earplug includes a central stem and a plurality of flange elements in the shape of umbrellas whose middle portions merge with the stem. U.S. Pat. No. 4,867,149 by Falco describes an earplug of this type, wherein each umbrella element is of hemispherical shape so that the peripheries of the elements extend parallel to the axis of the stem. Although such earplugs with hemispherical flange elements can provide protection against noise, their noise protection is limited. Also, as the earplug is removed, it can create a vacuum in the ear canal which can be painful to the user. An earplug of the type which has flange elements, which provided better noise protection and which was more comfortable to remove from the ear canal than prior earplugs with umbrella elements, would be of considerable value.

SUMMARY OF THE INVENTION

In accordance with one embodiment of the present invention, an earplug is provided, of the type that has hollow largely cone-shaped elements spaced along a stem, which provides enhanced sound protection and which provides more comfortable withdrawal of the earplug from the ear than heretofore. Each element has a peripheral portion extending with a radially outward and rearward directional component. As a result, when the peripheral portion is compressed in diameter by the ear canal of the wearer during forward movement into the ear canal, the peripheral portion tends to be deflected flat against the ear canal to provide large area contact therewith to seal out sound.

The radially outward and rearward directional components of the peripheral portion of a cone element, also is advantageous in causing the element to fold or curl forwardly when the earplug is pulled out of the ear. During such forward curling, a gap tends to be opened at the periphery of the element, which allows air to pass into the ear canal, to thereby minimize the creation of a vacuum in the ear canal that makes it uncomfortable to pull out the earplug.

The novel features of the invention are set forth with particularity in the appended claims. The invention will be best understood from the following description when read in conjunction with the accompanying drawings.

BRIEF DESCRIPTION OF THE DRAWINGS

FIG. 1 is a front and side isometric view of an earplug constructed in accordance with one embodiment of the present invention.

FIG. 2 is a sectional side view of the earplug of FIG. 1, taken perpendicular to the axis of the earplug.

FIG. 3 is a side elevation view of the earplug of FIG. 1.

DESCRIPTION OF THE PREFERRED EMBODIMENTS

Figure 4:
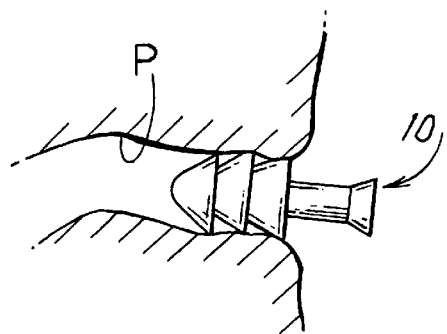
FIG. 4 is a side elevation view of the earplug of FIG. 1, showing it installed in the ear canal of a person.

FIG. 1 illustrates an earplug 10 of the present invention, which includes a stem portion or stem 12 extending along a stem axis 14, and three umbrella elements, or hollow cone elements 20–24 extending radially outwardly from the stem. The stem has forward and rearward end portions 26, 28, and the elements are spaced along the forward end portion. As shown in FIG. 2, each of the elements 20–24 is in the form of a truncated cone, with an apex end part or center portion, or forward end 30, 31, 33 of the truncated cone that merges with the stem, and with a base end part or peripheral portion, or rear end part 32, 35, 37 which lies rearward of the apex end part. The arrows F and R indicate forward and rearward directions, while arrows A denote radially outward directions that extend radially away from the axis 14. The umbrella or cone elements have largely, but not necessarily exactly, cone shapes, and may be referred to as cone elements. It can be seen in FIG. 2, which is a view taken perpendicular to axis 14, that the rear end part 32 of the front most cone element 24, overlaps a middle second cone element 22 that lies rearward of the front most cone element 24.

Applicant constructs the cone elements such as the first one 20, so its outside or peripheral portion 32A extends with rearward (R) and radially outward (A) directional components. In other words, each cone element, such as element 20, extends rearwardly (R) and radially outwardly (A) from its apex end part 33 along most of its axial length (along axis 14). Another way of describing this is that each cone element extends with rearward (R) and radially outward (A) directional components along most of the axial length of the cone element; that is, from its apex end part (30, 31, 33) to its rear end part (32, 35, 37). Another way of describing this is that the cone elements do not extend parallel to the axis 14, but extend at an incline or angle (B) to the axis, with the angle (B) being less than 90°, and with the direction of the incline being as shown in FIG. 2 (locations which lie progressively more rearward lie progressively further from said stem axis 14). This results in the peripheral portion 32A extending at an angle B from the axis 14, and having an included angle C, which are each a plurality of degrees. Preferably, the included angle C is between 45° and 100°, and most preferably between 50° and 85° which is about 60°. The included angle C is always several degrees less than 180° (preferably less than 120°) to assure that the peripheral portion extends with substantial radially outward and rearward directional components.

The earplug is a unitary molded earplug, that is molded of an easily deformed and resilient polymer, preferably an elastomeric material such as rubber having a durometer preferably between about 10 and 90 and more preferably about 40. This allows the peripheral portions of the cone elements to readily deform to a smaller outside diameter as the earplug is in a forward direction F inserted into the ear canal of a person. FIG. 4 shows the earplug 10 inserted into the ear canal P of a person, with the peripheral portions of the cone elements deflected radially inwardly.

Figure 5:
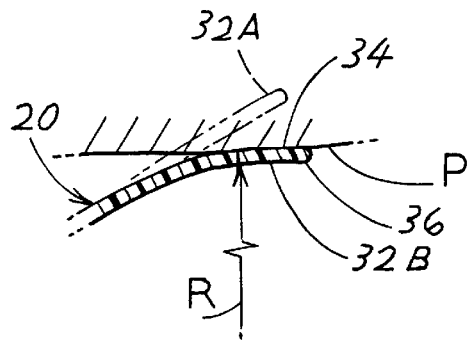
FIG. 5 is an enlarged view of the peripheral portion of a hollow cone element of the earplug of FIG. 4, showing the peripheral portion in its undeflected state and also in the configuration it assumes when deflected against the walls of the ear canal.

FIG. 5 is an enlarged view showing the peripheral portion 32A of one of the cone elements 20 in both the undeflected configuration at 32A and in the deflected configuration at 32B wherein it has been deflected against the walls P of the ear canal. The walls of the ear canal in FIG. 5 are shown as straight, although they generally have gentle curvatures. It can be seen that the deflected peripheral portion 32B has a large area of contact with the ear canal walls P, the contact being along substantially the entire region of the peripheral portion that originally lay at a radius R from the stem axis which was greater than the radius of the ear canal at that location. As a result, there is a wide area of contact between the outer surface 34 of the peripheral portion of the element, and the walls P of the person's ear canal. This wide area contact minimizes or eliminates gaps between the periphery of the element and the ear canal, through which sound can pass. Because of very small irregularity in the surface of a person's ear canal, there still may be tiny openings through which sound can pass, but they will be greatly reduced if not eliminated by the wide area of contact.

Figure 6:
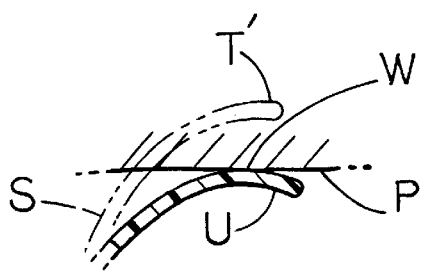
FIG. 6 is a view of a prior art earplug under the same circumstances as in FIG. 5.

FIG. 6 is an enlarged sectional view of a prior art earplug, such as the type described in U.S. Pat. No. 4,867,149, wherein the flange or umbrella element S was initially of hemispherical shape, with the peripheral portion T' extending parallel to the axis of the stem. When such peripheral portion is deflected radially inwardly, the peripheral portions U which lie forward of the initial point of contact V of the umbrella element with the ear canal P, tend to be curled radially inwardly as shown. This results in a smaller area of contact of the umbrella element peripheral portion, at W, with the walls of the ear canal. The smaller area of contact results in less complete sealing of the ear canal and therefore allows the transmission of a somewhat greater amount of sound. Applicant has constructed earplugs of the type shown in FIGS. 1–5 and compared them to prior art earplugs of the type shown in FIG. 6, and found that the type of deflection shown in FIGS. 5 and 6 do, in fact, occur. Applicant believes that the reason for the large area of contact shown in FIG. 5, is due to the relatively large inward deflection of the extreme periphery 36 of his cone element, resulting in a spring force tending to push it radially outwardly against the ear canal. In any case, the illustrated wide area of contact is found to occur.

Applicant finds that the cone shaped cone element, wherein the angle B remains substantially constant along the entire length of the element, provides good sound sealing qualities. An included angle C of about 60° provide very good sealing. An angle C of much more than about 60° can still be useful, but results in very large deflection of the extreme peripheral portion of the element, which can lead to undulation through which sound can pass. An included angle C of much less than 600 results in less inward deflection for the peripheral portion, which may result in not as great an area of contact, although it still can result in greater area of contact than for the prior art umbrella element indicated in FIG. 6.

Another advantage that applicant has found to using a cone element with a rearwardly expanding peripheral portion, is in breaking the vacuum during withdrawal of the earplug from the ear of the wearer. If the periphery of one or more cone elements seals tightly against the walls of the ear canal, then when the earplug is pulled out of the ear, it creates a vacuum in the ear until the seal(s) at the peripheral portions of the elements are broken. A temporary vacuum created during pullout of the earplug can be uncomfortable or even painful.

Figure 7:
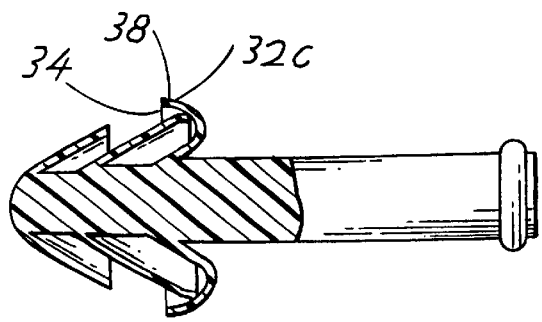
FIG. 7 is a sectional view of the earplug of FIG. 2, shown with one cone element folded back into a reverse configuration.

Applicant finds that the present cone elements with rearwardly expanding peripheral portions, have a decided tendency to fold forwardly as shown in FIG. 7 when pulled out of the ear. In that case, the formerly outer surface 34 of the peripheral portion, when in its reverse configuration 32C, lies radially inward of the formerly inner surface 38 of the element. During the turnover of the peripheral portion, a gap tends to be temporarily created between the peripheral portion of the element and the walls of the ear canal. This appears due to not all locations along the periphery folding over at the same time. This air gap tends to be created after the earplug has been moved rearwardly a moderate distance, after the vacuum has been created. By breaking the vacuum, applicant makes pullout of the earplug more comfortable.

It may be noted that after the peripheral portion has achieved its reverse configuration, it may form a seal against the walls of the earplug, so that continued pullout of the earplug can again create a vacuum. However, the degree of vacuum will be less than otherwise because the vacuum was broken after it was initially created. Applicant prefers that the earplug be inserted only far enough to seal against the walls of the ear canal, so that when the earplug is pulled out, it is pulled only a short additional distance before complete breaking of the seal between the folded-over peripheral portion and the ear canal.

Applicant can form the rearward end of the stem so it is a cylindrical extension of the middle of the stem. However, this requires the user to grasp the cylindrical portion in pushing the earplug into the ear. Applicant prefers to form the rearward portion with a solid rounded flange-like projection 40 (FIG. 2) at the rear end. The flange or projection 40 is preferably of substantially semicircular cross-sectional shape and lies on the cylindrical portion 41 of the stem. During installation of the earplug, a person can press the tip of his index finger against the rear end 44 of the stem, and press gently forwardly to insert the earplug. The rounded flange 40 facilitates removal of the earplug from the ear by preventing slipping of the fingers off the rear end of the stem, while providing a comfortable rounded surface to grasp. The diameter F' at the flange is less than the greatest diameter G of the middle cone element 22.

Applicant has constructed and tested earplugs of the relative size and shape shown in FIGS. 1–5 and 7. The earplug has an overall length of 33 mm, a stem rearward end portion diameter D of 5.5 mm and radius R of 2.75 mm. The first cone element 20 which is the rearmost one and has the largest diameter, has a greatest diameter E of 14 mm. Thus, the rearward portion stem diameter D is less than one half the largest element diameter E. The flange 40 has a diameter F' of 7 mm, with its periphery forming half of a circle (in the sectional view of FIG. 2A). The earplug is constructed of rubber having a durometer of about 40, with the walls of the cone elements having an average thickness T which is preferably between 0.4 mm and 1.0 mm, with the actual thickness T being about 0.7 mm. The thickness T of 0.7 mm is 5% of the element diameter E, and the thickness of each cone element is preferably no more than about 7% (i.e. is less than 10%) of the diameter E (14 mm) of the first element, and preferably no more than 5% of the diameter E.

Figure 8:
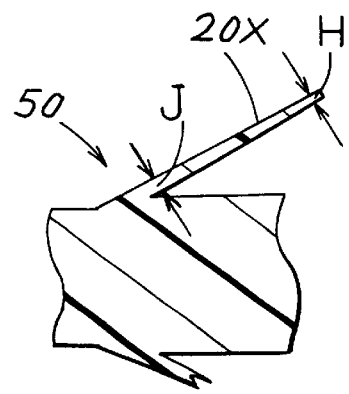
FIG. 8 is a partial sectional view of an earplug constructed in accordance with another embodiment of the invention wherein the wall thickness of an element is tapered.

FIG. 8 illustrates a portion of another earplug 50 of a construction that is the same as those of FIGS. 1–5 and 7, except that the cone element 20× is tapered in thickness, with the thickness H at the peripheral portion, which will deflect against the ear canal, being less than the thickness J at the center portion of the element near where it merges with the stem 52. In one earplug that applicant has designed, the peripheral portion had a thickness H of about 0.2 mm, while the center portion J had a thickness of about 0.7 mm which is more than twice as great. The advantage of this construction is that the thin peripheral portion more readily conforms to the ear canal and with lower pressure there against, to increase comfort. The thicker center portion supports the peripheral portion to press it radially outwardly against the ear canal.

Thus, the invention provides an earplug of the type having a stem and at least one and preferably a plurality of cone elements centered on the stem, which provides enhanced sound sealing and increased comfort during removal of the earplug from the ear canal. This is accomplished by forming a first element, and preferably all of them, so the peripheral portions extend with both radially outward and rearward directional components. The angling of the peripheral portions preferably results in an included angle that is preferably about 60°. With the rearward portion of the stem having a diameter less than half the greatest diameter of the earplug, the rearward portion includes a rounded flange or enlargement at its rear end. The cone elements can be formed of conical shape, so the included angle is constant along the length of the element. The walls of an element can be tapered in thickness, so the peripheral portion has a smaller thickness, preferably less than half the thickness, of the center portion of the element.

The novel features of the invention are set forth with particularity in the appended claims. The invention will be best understood from the following description when read in conjunction with the accompanying drawings.

What is claimed is:

1. An earplug comprising:

a unitary molded earplug having an axis that extends in forward and rearward directions, having an elongated central stem portion which extends along said axis and which has forward and rearward stem portion ends, and having a plurality of hollow truncated cone elements including a first cone element, with each of said cone elements having an apex end part merging with said stem portion and having a rear end part with an extreme rear end, and with each cone element extending with rearward (R) and radially outward (A) directional components from its apex end part along most of the axial length of the cone element to its extreme rear end, said apex end parts of said cone elements being spaced apart along said stem;

said rear end part of said first cone element having a maximum thickness which is no more than 7 percent of the diameter of said extreme rear end, and said cone rear end part having an outer surface forming an included angle of between 50° and 85° as seen in a sectional view taken perpendicular to said axis.

2. The earplug described in claim 1 wherein:

said rearward end of said stem is substantially in the form of an elongated cylinder but includes a band means of a largely semicircular cross-section extending around said cylinder to aid in grasping said stem rearward end, with said semicircular cross-section completely filled with solid material and having diametrically opposite sides that both lie substantially on said cylinder which forms said stem, and with the area radially outside and immediately forward of said band means being completely unobstructed so a person can easily grasp said cylinder at a location immediately forward of said band means.

3. An earplug comprising:

an elongated stem having forward and rearward end portions and having an axis that extends in forward and rearward directions;

a plurality of cone elements each having an axis coincident with said stem axis, with each element having a center portion merging with said stem at locations spaced along said forward end portion of said stem, so a first of said elements lies rearward of at least one other element, and with each element having a peripheral portion lying rearward of its center portion;

said peripheral portion of said first cone element extending with rearward and radially-outward directional components, so that locations on said peripheral portion which lie progressively more rearward lie progressively further from said stem axis;

said peripheral portion of said first element has an outer surface that diverges at an included angle of about 60°, as seen in a sectional view taken perpendicular to said stem axis.

4. The earplug described in claim 3 wherein:

said first element has a rear end with a diameter (E) of about 14 mm, and said first element has walls of a thickness Cr) of about 0.5 mm.

5. A method for forming, installing. and removing an earplug in the ear canal of a person, comprising:

forming an earplug that includes a stem with a stem axis and with forward and rearward stem end portions, and a plurality of hollow cone elements each having a cone axis coincident with said stem axis and with each element expanding in radius in a rearward direction with a first of said elements expanding at an included angle of about 60°, with said elements having middle portions merging with said stem and spaced apart along said forward portion of said stem, and with said elements each having a peripheral edge portion;

inserting said earplug forward stem portion and said cone elements thereon into an ear canal of a person, with the edge portion of at least a first of said cone element engaging the ear canal and deflected toward said stem axis;

pulling on said stem rearward portion to pull said earplug out of said ear canal, including dragging said peripheral edge portion of said first cone element along said ear canal until said edge portion folds back to pull said first element into a reverse configuration wherein it generally expands in a forward direction.

\* \* \* \* \*